United States Patent [19]
Cohen

[11] Patent Number: 5,314,456
[45] Date of Patent: May 24, 1994

[54] THERAPEUTIC PAD FOR RELIEF OF HEADACHE-RELATED HEAD, TEMPLE, NECK AND BACK PAIN

[76] Inventor: Gary M. Cohen, 9694 Sun Pointe Dr., Boynton Beach, Fla. 33437

[21] Appl. No.: 34,831

[22] Filed: Mar. 19, 1993

[51] Int. Cl.$^5$ .............................................. A61F 7/00
[52] U.S. Cl. .................... 607/109; 607/110; 607/112
[58] Field of Search ............... 128/399–403; 607/108–110, 112

[56] References Cited

U.S. PATENT DOCUMENTS

| | | | |
|---|---|---|---|
| 4,382,446 | 5/1983 | Truelock et al. | 128/402 |
| 4,607,624 | 8/1986 | Jefferson | 128/399 |
| 4,765,338 | 8/1988 | Turner et al. | 128/402 |
| 4,781,193 | 11/1988 | Pagden | 128/402 |
| 4,891,501 | 1/1990 | Lipton | 128/399 |

*Primary Examiner*—Kyle L. Howell
*Assistant Examiner*—Robert L. Nasser, Jr.
*Attorney, Agent, or Firm*—M. K. Silverman

[57] ABSTRACT

A therapeutic pad for relief of headache-associated head, temple, neck and upper back pain includes a lower portion substantially defining, in surface geometry, a rectangle having major and a minor bases and, further, having an axis of symmetry co-parallel to the minor bases. The therapeutic pad also includes an upper portion substantially defining, in surface geometry, an elongate wing-like shape having a major axis of about double the length of the major bases of the rectangle of the lower portion, and having a minor axis which is an axis of symmetry co-linear to the axis of symmetry of the lower portion. The upper portion includes elements for selectably securing to each other portions of lateral ends of the wing-like shape. The therapeutic pad also includes a connecting portion defining an isthmus between the lower and upper portions, the geometry of the connecting portion having an axis of symmetry co-linear with the axes of symmetry of the upper and lower portions, the connecting portion also having a major axis trans-verse to its axis of symmetry, said major axis having a length of about one-half of the major bases of the rectangle of the lower portion. The therapeutic pad is provided with elements for providing therapeutic inputs, which are embedded within each of the portions of the pad.

8 Claims, 5 Drawing Sheets

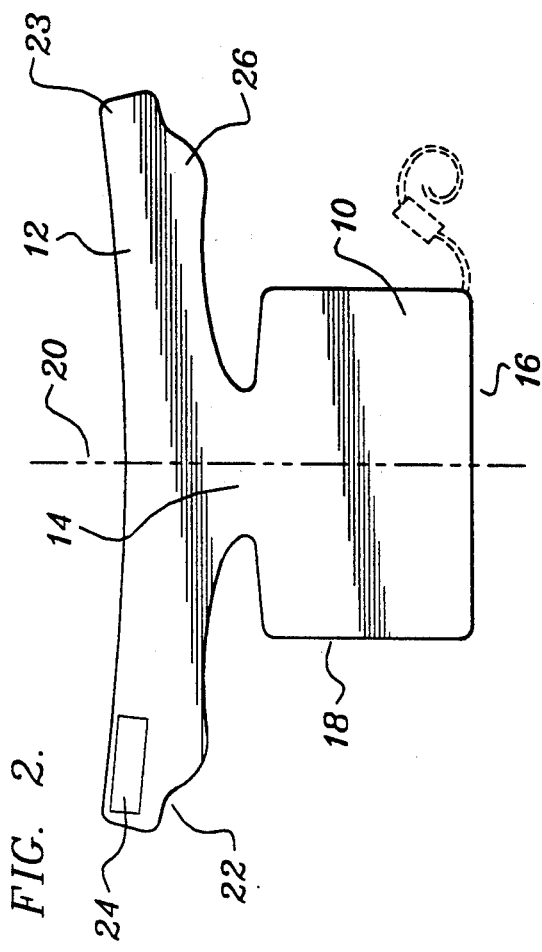
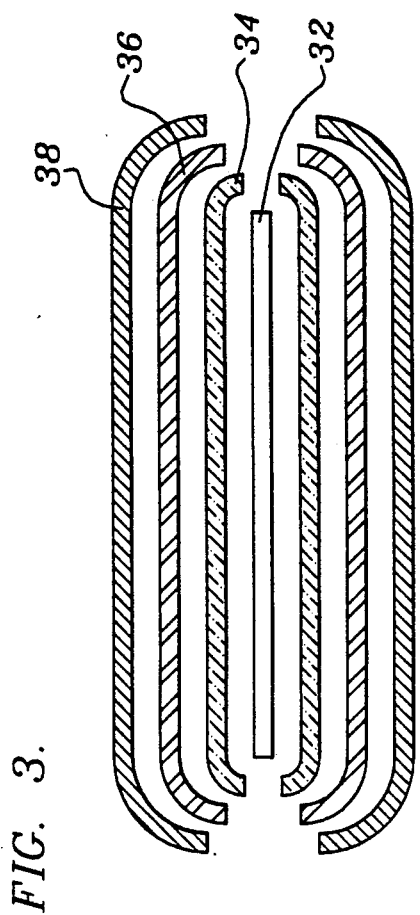
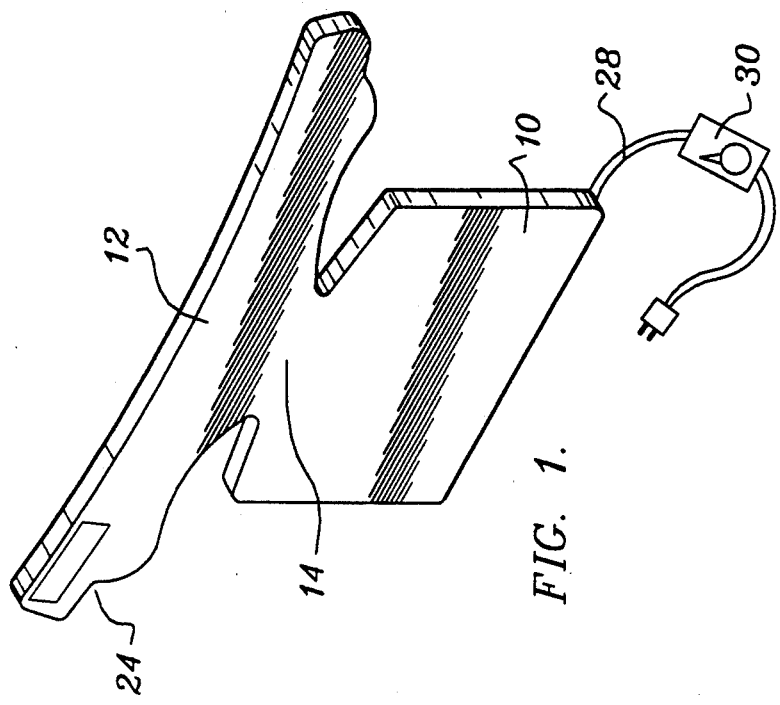

THERAPEUTIC PAD FOR RELIEF OF HEADACHE-RELATED HEAD, TEMPLE, NECK AND BACK PAIN

BACKGROUND INVENTION

The present invention relates to therapeutic pads and, more particularly, pads in the nature of heating or cooling pads particularly configured for relief of pain of the head, neck, and upper back.

In the prior art of therapeutic pads it is known to provide devices in the nature of a heating pad which completely or substantially envelop the head. Such devices are effectively a hood which is pulled over the entire head in the use thereof. This prior art is reflected in U.S. Pat. No. 3,134,891 (1964) to Hyer, entitled Neck and Face Dry Heat Applicator; U.S. Pat. No. 4,061,898 (1977) entitled Heat Cap; and U.S. Pat. No. 5,129,391 (1992) entitled Thermal Packs.

Other prior art of the instant type provides heating to the back, shoulders, and upper chest, but not to any part of the head. Such art is reflected in U.S. Pat. No. 2,718,585 (1955) to Hariu, entitled Heating Pads and U.S. Pat. No. 3,839,621 (1974), also to Harui, entitled Body Heating Device.

It is also known to configure heating pads and the like for the purpose of providing heat or cold to the shoulders and adjacent tissues only. Such art is reflected in U.S. Pat. No. 4,742,827 (1988) to Lipton, entitled Heating Pad.

There, as well, exist various and sundry other efforts in the art to provide heating directed to one or another particular portion of the human anatomy. However, there does not, to the knowledge of the within inventor, exist any heating, cooling, or vibratory pad configured and structured to address those particular anatomical factors, namely, those particular combinations of neural, arterial and muscle groups which play a primary role in the cause of headaches, including migraine headaches.

The present invention therefore constitutes an effort to address the long-felt need for a therapeutic pad, the configuration and function of which is particularly adapted to provide relief to sufferers of headaches by affording targeted therapeutic inputs to anatomic factors in the head, neck, and upper back that are associated with the cause of headache pain.

SUMMARY OF THE INVENTION

The present invention constitutes a therapeutic pad for relief of headache-associated head, temple, neck and upper back pain. The pad, more particularly, comprises a lower portion substantially defining, in surface geometry, a region having a major and a minor axis and, further, having an axis of symmetry co-linear to said minor axis. The therapeutic pad further includes an upper portion substantially defining, in surface geometry, an elongate wing-like shape having a major axis of about double the length of said major axis of said lower portion, and further having a minor axis comprising an axis of symmetry co-linear to said axis of symmetry of said lower portion. Said upper portion includes means for selectably securing to each other areas of the lateral ends of said wing-like shape. The therapeutic pad also includes a connecting portion defining an isthmus between said lower and upper portions, the geometry of said connecting portion having an axis of symmetry co-linear with said axes of symmetry of said upper and lower portions, said common portions also having a major axis transverse to its axis of symmetry, said major axis having a length of about one-half of said major axis of said lower portion. The therapeutic pad is provided with means for providing therapeutic inputs which are embedded within each of said portions, which means may be in the nature of hot, cold or vibratory stimuli. Such stimuli are provided simultaneously and substantially uniformly to all surfaces of each of said portions of the therapeutic pad.

It is accordingly an object of the present invention to provide a therapeutic pad for the relief of headache-related head, neck, and upper back pain.

It is another object of the invention to provide a therapeutic pad particularly configured to furnish stimuli to neural, arterial and muscular centers associated with headache, including migraine, pain.

It is a further object of the present invention to provide a therapeutic pad of the above type which may be conveniently and safely employed by lay persons.

It is a yet further object of the invention to provide a therapeutic pad of the above type which particularly addresses the light-sensitivity of persons suffering from headache-related and migraine pain.

The above and yet other objects and advantages of the present invention will become apparent from the hereinafter set forth Brief Description of the Drawings, Detailed Description of the Invention, and claims appended herewith.

BRIEF DESCRIPTION OF THE DRAWINGS

FIG. 1 is a perspective view of the inventive therapeutic pad.

FIG. 2 is a front elevational view thereof.

FIG. 3 is a cross-sectional schematic view of the therapeutic input means associated with a dry heat embodiment of the instant invention.

DETAILED DESCRIPTION OF THE INVENTION

Figure 4:
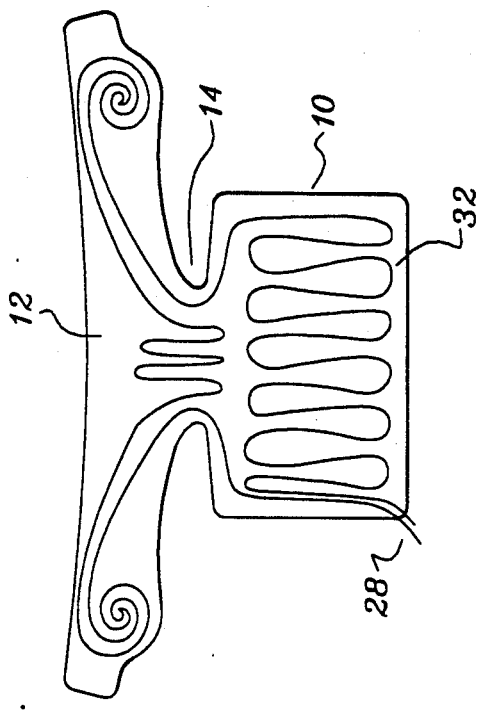
FIG. 4 is an internal wiring diagram of said dry heat embodiment of the present invention.

With reference to the perspective and front views of FIGS. 1 and 2 there is show the generalized geometry of the present inventive therapeutic pad for relief of headache and related head, neck, and upper back pain. In said figures the inventive therapeutic pad may be seen to include a lower portion 10, an upper portion 12, and a connecting portion 14 which is in the nature of an isthmus which integrally connects the upper and lower portions of the pad.

As may be particularly noted in FIG. 2, said lower portion 10 defines, in surface geometry, a rectangle having major and minor bases 16 and 18 respectively. It is to be understood that, in an alternative embodiment, the lower portion 10 may take the form of an oval having a major axis substantially equal in dimension to said major base of lower portion 10 and having a minor axis substantially equal in dimension to said minor base 18 of lower portion 10.

A further defining aspect of said lower portion 10 is its symmetry about line of symmetry 20 which also comprises, as is more fully set forth below, a line of symmetry for the geometry of the entire pad.

With further reference to FIG. 2 said upper portion 12 may be seen to define, in surface geometry, an elongate wing-like shape having a major axis, that is, a horizontal axis, having approximately twice the aggregate length of said major base 16 of said lower portion 10. Further, said wing-like shape of upper portion 12 is symmetric about said line of symmetry 20. It should be further noted with reference to upper portion 12 that the outermost lateral areas 22 and 23 are provided with means, for example, VELCRO strips 24 which may be employed for selectably securing respective lateral areas 22 and 23 of upper portion 12 to each other. In the views of FIG. 1 and 2 the VELCRO strip at lateral end 23 of upper portion 12 is not visible in that when the therapeutic pad is secured to the human head in the fashion shown in FIGS. 5 and 6 it is necessary to place the respective VELCRO strips on opposite sides of upper portion 12 to provide for proper securement of the VELCRO strips to each other. Because of the horizontal length of each VELCRO strip 24, the upper portion 12 of the therapeutic pad may be secured about the circumference of the head of a user any size.

It is also noted, with reference to upper portion 12, that the lower perimeter thereof is provided with bulges 26 in order to, as is set forth below, provide cover for the eyes of a user.

Located between said upper and lower portions of the therapeutic pad is said connecting portion 14. Its geometry may be views as isthmus between the upper and lower portions. The geometry of the connecting portion 14 is such that the greatest horizontal dimension thereof corresponds to approximately one-half of the length of said major base 16 of lower portion 10. Further, said connecting portion 14 is, as is the case with said upper and lower portions, symmetric relative to line of symmetry 20.

With further reference to FIGS. 1 and 2, the inventive pad may be seen to also include extension cord 28 and power level control 30. This control provides for standard selection between low, medium, and high power levels. As is more fully set forth below it is to be appreciated that while the use of an alternating current power supply constitutes the preferred embodiment of the invention, the invention may also be practiced through the use of other power or energy means including batteries and chemical gels for the provision of either heat or cold.

With reference to the cross-sectional schematic view of FIG. 3, the generalized construction of the alternating current power embodiment is shown. More particularly, in FIG. 3 is shown a resistive heating element 32, a felt or other insulative layer 34, a high-temperature resistive plastic shrink-wrap layer 36, and an external cotton layer 38. This construction reflects the standard state of the art construction of alternating current powered heating pads.

With reference to the view of FIG. 4 there is shown the configuration in which electrical resistive heating element 32 is laid-out within the geometry of the therapeutic pad. As may be noted in said figure, the locations of the heating element 32 reflect the specific medical-/anatomical objectives as are more fully set forth below, namely, provision of therapeutic stimuli to the eyes, temples, neck, and upper back.

Figure 6:
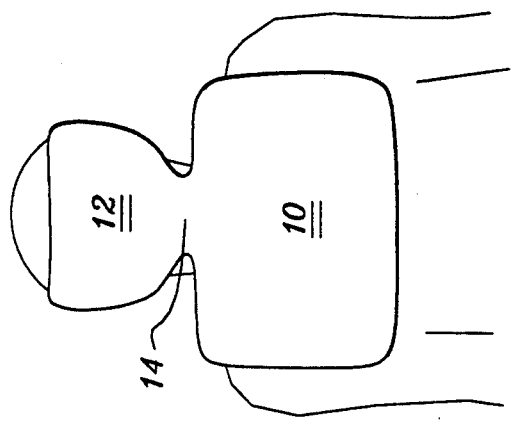
FIG. 6 is a back view showing the appearance of the therapeutic pad relative to the view of FIG. 5.
Figure 5:
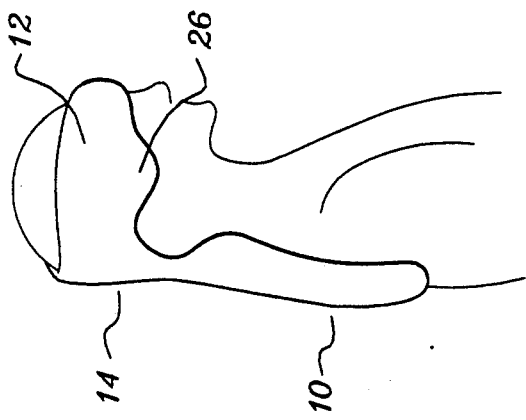
FIG. 5 is a side view showing the appearance of the therapeutic pad in use.

In the views of FIGS. 5 and 6, it is seen that the inventive pad when affixed to the human head through the use of said VELCRO strips 24 of upper portion 12 will completely cover the eyes, temples, back of the head, back of the neck, and upper back of the user.

Figure 7:
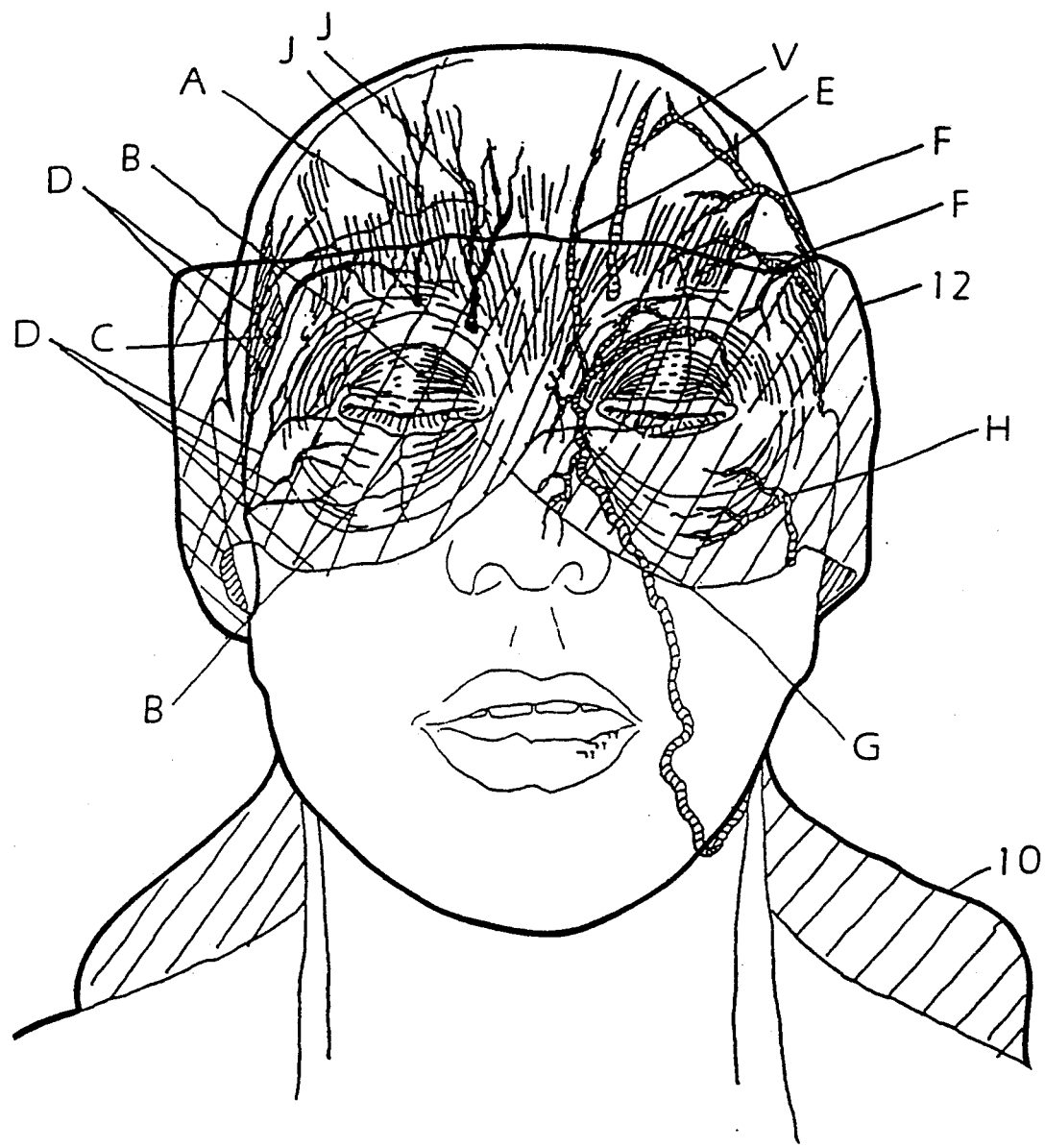
FIG. 7 is a front enlarged anatomical view showing the anatomical factors affected through usage of the inventive pad.
Figure 8:
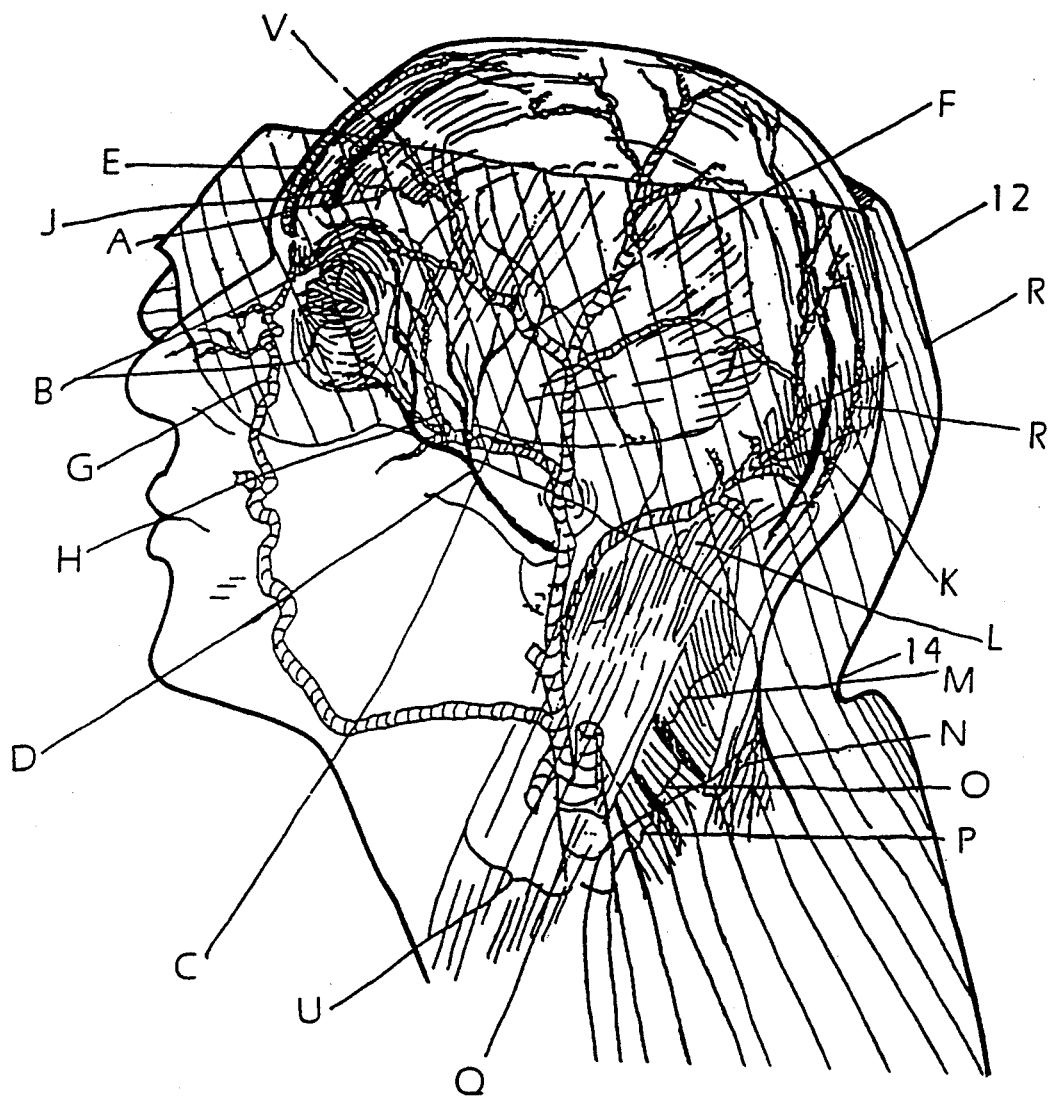
FIG. 8 is a view of the type of FIG. 7 taken from the side of the human face and neck.
Figure 9:
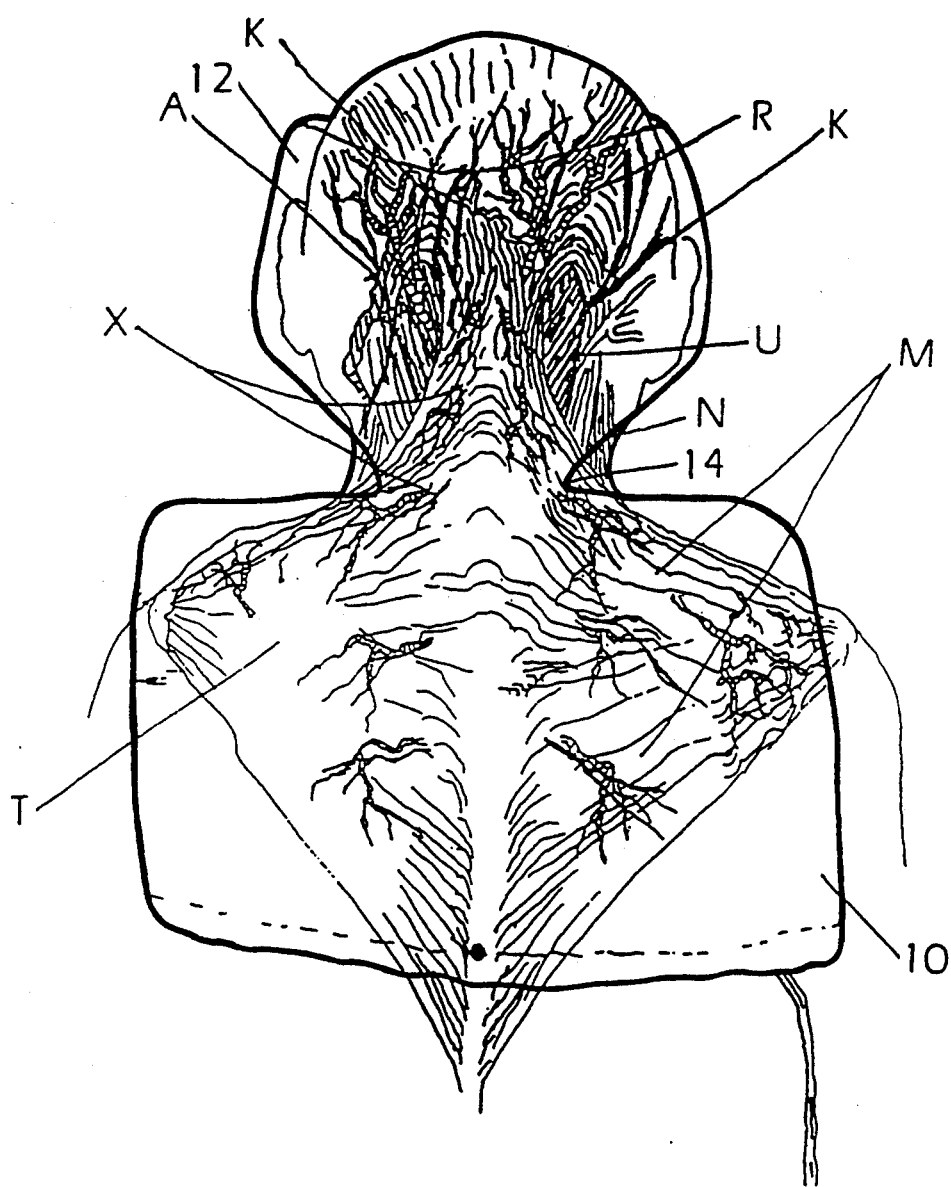
FIG. 9 is an anatomical view of the type of FIGS. 7 and 8, taken from the back of the user.

With regard to the anatomical views of FIGS. 7 thru 9 there is shown therein the various groups of neural, arterial, and muscular factors associated with the so-called pain centers of headache and neckache pain.

With reference to the ocular area (see FIG. 7) the upper portion 12 of the therapeutic pad may be seen to cover the entire orbital region including the frontal portion of the orbital frontalis muscle A, the orbicularis oculi muscle B, the temporalis muscle C (more fully shown in FIG. 8), the facial nerve D, and supraorbital nerve J.

Shown to the right of the front facial view of FIG. 7 is the facial artery G and its upper extension known as the angular artery E. Shown to the right of angular artery E is supraorbital artery V, and to the right thereof the frontal branch of the superficial temporal artery F. Shown beneath the eye of the user is the zygomaticoorbital artery H.

The emphasis of the present invention upon the nerves, arteries and muscles of the ocular area reflects the fact that many forms of headache have been determined to be related to irritation of the eyes and, more particularly, to light sensitivity which occurs during periods of headache, including migraine headache, discomfort. Accordingly, through configuration of the instant therapeutic pad to provide complete coverage of the ocular area, this including all neural, arterial, and muscular support thereof, there is provided an increase of blood supply and generalized relaxation of muscles relative to all of these anatomical elements in a uniform fashion.

With reference to the side anatomical view of FIG. 8, there are shown all of the above referenced nerves, arteries, and muscles. However, there is also shown the greater occipital nerve K, the upper attachment of the sternocleidomastoid muscle L of the upper neck, the levator scapulae muscle M beginning at the upper neck, the trapezius muscle N of the neck, the scalenus posterior muscle O of the neck and the scalenus medius muscle P of the neck and upper back. Further shown is the common carotid artery Q, the occipital artery R (note, several branches thereof), and the sternocleidomastoid muscle U.

It may be noted that the portion of the therapeutic pad which is adjacent to the axis of symmetry 20 (see FIG. 2) provides therapeutic values to numerous anatomical areas of the back of the head, back of the neck, and upper back. It is to be also noted that the carotid artery Q extends upwardly from the neck to many areas of the side, front, and back of the skull, and that the occipital artery R branches from the lower portion of the carotid artery Q. Thereby, by providing therapeutic values to the carotid and occipital arteries, an increase of blood supply to all of the associated muscle and nerve groups, for example, the greater occipital nerve K and the various neck muscle groups is assured.

With reference to the back anatomical view of FIG. 9, there is additionally shown the rhomboid major muscle T, and the is lesser occipital nerve X. Also shown in FIG. 9 is the posterior view of the above referenced greater occipital nerve K, occipital artery R, trapezius M (which covers most of the upper back), levator scapulae muscle N, and sternocleidomastoid muscle U. By the provision of therapeutic values to the upper back in the manner shown in FIGS. 5, 6, 8, and 9, blood supply is enhanced to all of the arterial, muscle and nerve groups thereabove, that is, all anatomical groups of the neck and head.

Further, the application of heat to the upper spinal cord (not shown in the figures) will, of course, afford a soothing effect to the entire nervous system. Accordingly, those areas of the body, namely, eyes, temple, base of skull, and upper back which have been identified as pain centers associated with headache pain, including migraine, and neck ache pain, are all addressed in the inventive therapeutic pad as set forth above. Accordingly, through the application of heat, dilation of all pertinent arterial groups is assured and with it the provision of increased oxygen to the muscles, relaxation of muscles, and removal of lactic acid therefrom.

Further, with such effects is afforded a decrease in neural activity including particularly activity of the cranial nerves, the facial nerve D and the trigeminal nerve (associated with the optic nerve) which will thereby provide direct signalling to the brain that a decrease in pain has occurred. Accordingly, the integrated effect of the invention should be understood to be one of providing increased blood to muscles, reduction of lactic acid therein, and decrease in activity of the facial, trigeminal, and occipital nerves. It is also noted that the temporalis muscle C (see FIGS. 7 and 8) is innervated by the trigeminal nerve thereby giving rise to the well-known headache pain otherwise centered in the temple.

With regard to the manner of operation of the invention, it is to be appreciated that, within the scope of the present invention, alternatives to the use of an alternating current power source may be provided. For example, there are, within the state-of-the-art, many heating and cooling gels (see for example U.S. Pat. No. 5,129,391 to Brodsky) which provide for heating or cooling and which may be activated simply by placing the unit in a microwave, in the case of a heating gel, or placing the therapeutic pad in a freezer compartment of a refrigerator, in the case of a cooling gel. Also, within the scope of the present invention, may be provided vibratory means used in association with heating or cooling means.

The present therapeutic pad, in construction, is also provided with all of the thermostatic and anti-inflammatory safety features which are typical in the state-of-the-art heating pads.

Accordingly, while there has been shown and described the preferred embodiment of the present invention it is to be appreciated that the invention may be embodied otherwise than is herein specifically shown and described and that, within said embodiment, certain changes may be made in the form and arrangement of the parts without departing from the underlying ideas or principles of this invention within the scope of the claims as appended herewith.

Having thus described my invention what I claim as new, useful and non-obvious and, accordingly, secure by Letters Patent of the United States is:

1. A therapeutic pad for the relief of headache-related pain of the head, eyes, temples, base of the skull, neck and upper back, the pad comprising:
   (a) a lower portion substantially defining, in surface geometry, a region having a major axis and a minor axis, and an axis of symmetry co-linear to said minor axis;
   (b) an upper portion substantially defining, in surface geometry, an elongate wing-like shape having a major axis of about double the length of said major axis of said lower portion, and having a minor axis comprising an axis of symmetry of said upper portion, said axis of symmetry co-linear to said axis of symmetry of said lower portion said upper portion, said upper portion having a first and second lateral end, said upper portion also including means for selectably securing to each other said first and second lateral ends thereof;
   (c) a connecting portion defining an isthmus between said lower and upper portions, the geometry of said connecting portion having an axis of symmetry, colinear with said axes of symmetry of said upper and lower portions, said connecting portion also having a major axis, transverse to its axis of symmetry, having a length of about one-half of the length of said major axis of said lower portion; and
   (d) means, embedded within each of said portions for selectably providing simultaneous and substantially uniform therapeutic stimuli to all surfaces of said portions.

2. The therapeutic pad as recited in claim 1 in which said therapeutic stimuli comprises heat means.

3. The therapeutic pad as recited in claim 1 in which said therapeutic stimuli comprise negative thermal value means.

4. The therapeutic pad as recited in claim 1 in which said therapeutic stimuli comprise vibratory means.

5. The therapeutic pad as recited in claim 2 in which said therapeutic stimuli comprise vibratory means.

6. The therapeutic pad as recited in claim 1 in which said said lower portion comprises a rectangle having minor bases so parallel with said minor axis and major bases parallel with said major axis of said lower portion.

7. The therapeutic pad as recited in claim 2 in which said lower portion comprises a rectangle having minor bases parallel with said minor axis and major bases parallel with said major axis of said lower portion.

8. The therapeutic pad as recited in claim 7 in which said therapeutic stimuli comprises vibratory means.

* * * * *